United States Patent [19]

Biegeleisen-Knight et al.

[11] Patent Number: 5,148,809

[45] Date of Patent: Sep. 22, 1992

[54] METHOD AND APPARATUS FOR DETECTING BLOOD VESSELS AND DISPLAYING AN ENHANCED VIDEO IMAGE FROM AN ULTRASOUND SCAN

[75] Inventors: Robert M. Biegeleisen-Knight, Boca Raton; Keith A. Duke, West Palm Beach, both of Fla.

[73] Assignee: Asgard Medical Systems, Inc., Boca Raton, Fla.

[21] Appl. No.: 486,603

[22] Filed: Feb. 28, 1990

[51] Int. Cl.$^5$ ............................................. A61B 8/00
[52] U.S. Cl. ................................. 128/660.07; 358/112
[58] Field of Search ............. 128/112, 660.01, 660.04, 128/660.05, 660.06, 661.10, 653, 696; 358/111, 112, 169

[56] References Cited

U.S. PATENT DOCUMENTS

| | | | |
|---|---|---|---|
| 4,630,612 | 12/1986 | Uchida et al. ................. | 128/660.05 |
| 4,692,864 | 9/1987 | Shimoni et al. ............. | 128/660.07 X |
| 4,761,740 | 8/1988 | Lipschutz ................. | 128/660.05 X |

FOREIGN PATENT DOCUMENTS 2447396 4/1976 Fed. Rep. of Germany ...... 128/695

OTHER PUBLICATIONS

Andrews, H. C. et al "Image Processing by Digital Computers", IEEE Spectrum Jul. 1972 pp. 20-32.

*Primary Examiner*—Francis Jaworski
*Attorney, Agent, or Firm*—Eckert, Seamans, Cherin & Mellott

[57] ABSTRACT

The system for detecting blood vessels and displaying an enhanced video image from video images obtained from an ultrasound scanner includes, in one embodiment, a target filter which limits the area in the video image to a predetermined size and an edge detector which senses gradients in pixel values in that target area. The edge detector marks transitional pixels at gradients exceeding a certain level. The system also includes a monitor for displaying the video image obtained from the ultrasound scanner. The marked transitional pixels are displayed in a contrasting color compared to the concurrently displayed input video image. In one embodiment, the target filter detects motion by comparing moving image block target areas separated in both time and space, counting moving image blocks and further limiting the target area to areas having the highest number of moving image blocks. Accordingly, smaller target areas are processed with the edge detector. In another embodiment, the target filter includes a gross edge detector, a transitional pixel counter and a further target filter which prioritizes the various the initial target areas such that the target area having the highest number of maaraked pixels is selected as the area to be further processed by the edge detector. In both embodiments, the electronic processing occurs in real time. A method is disclosed for detecting blood vessels and displaying an enhanced video image from a plurality of video images obtained from an ultrasound scanner.

15 Claims, 8 Drawing Sheets

FIG. 6
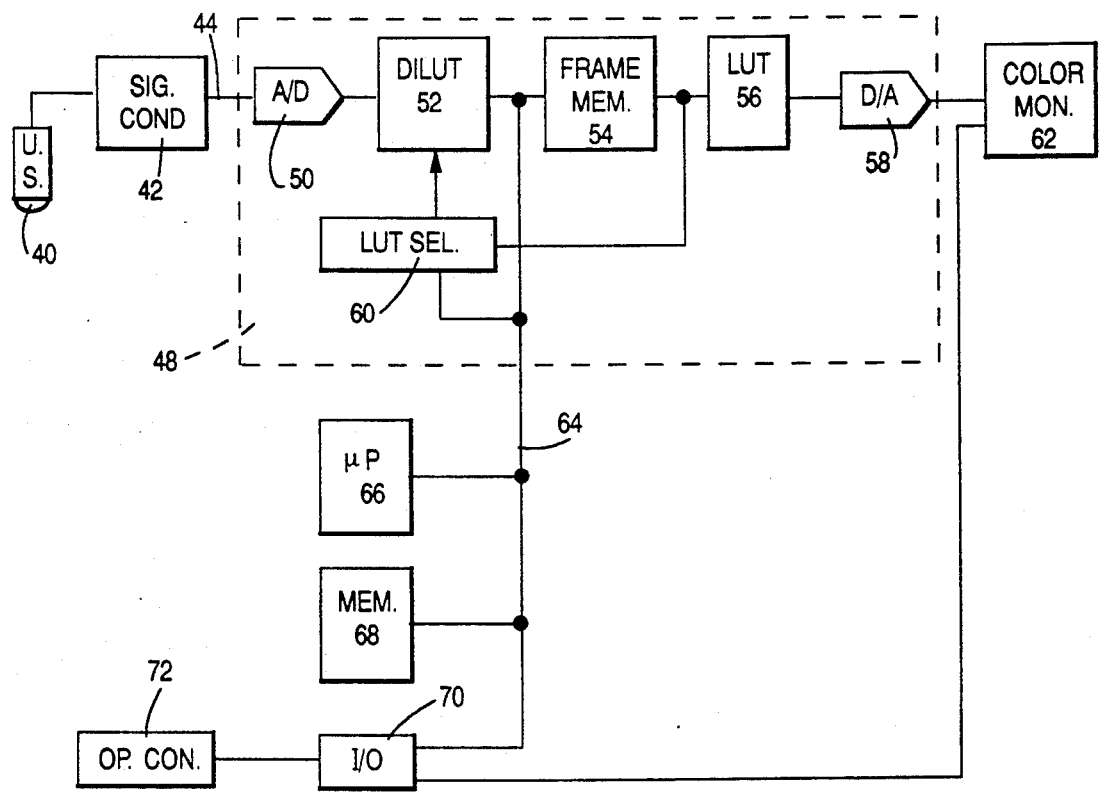
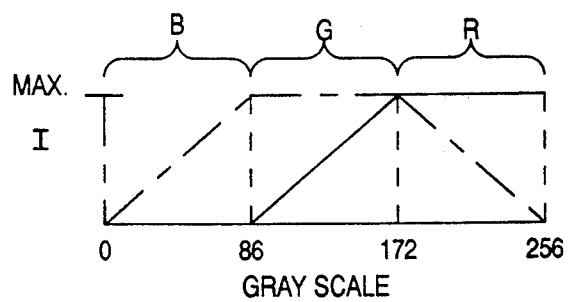
FIG. 7
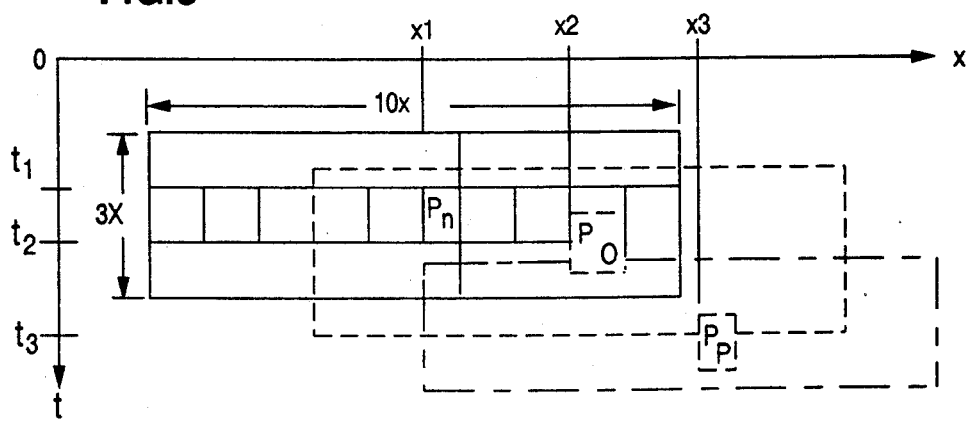
FIG. 8

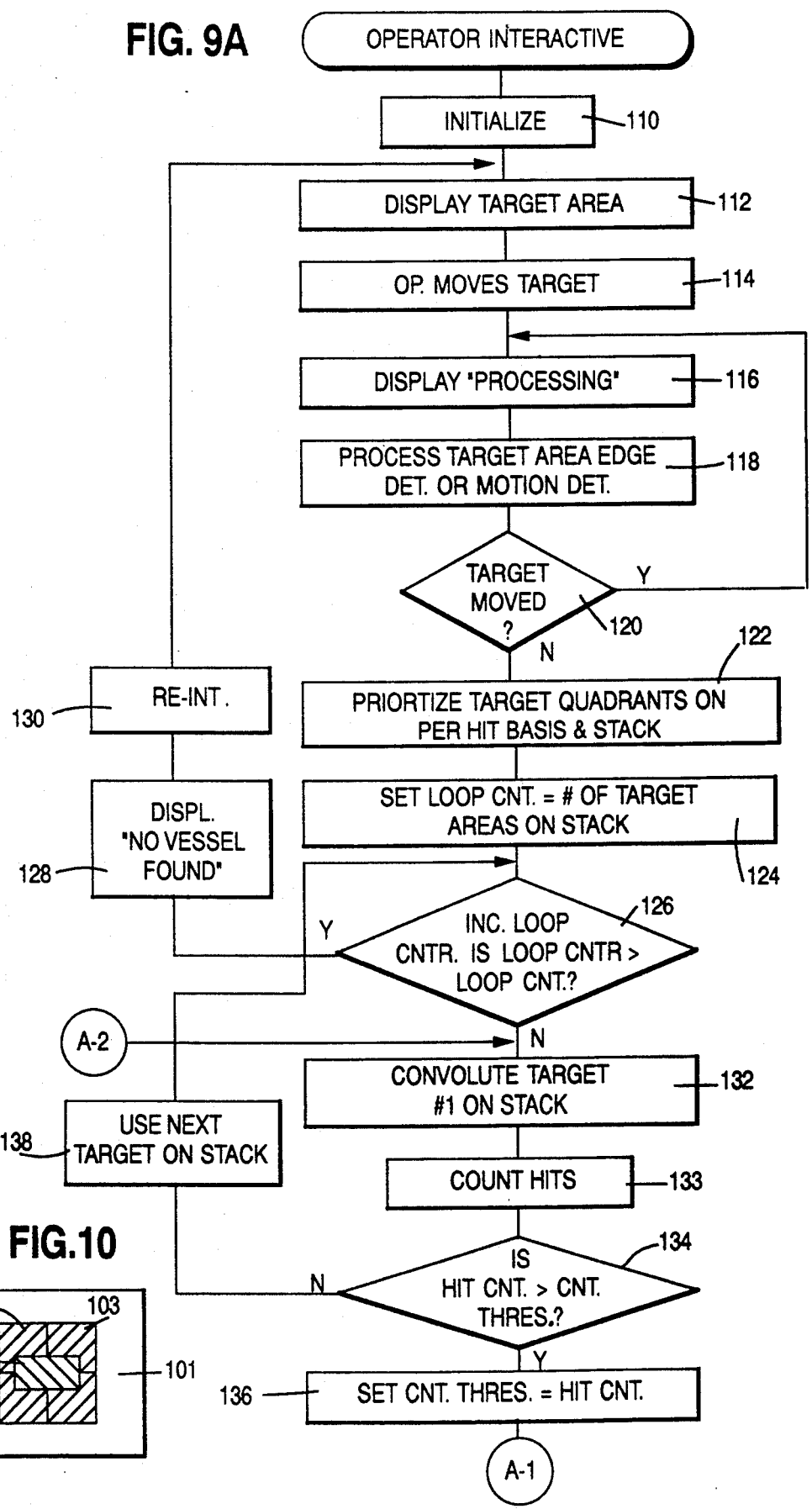
FIG. 9A
FIG. 10
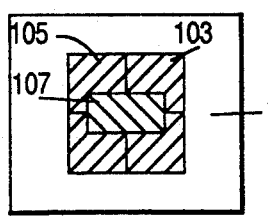

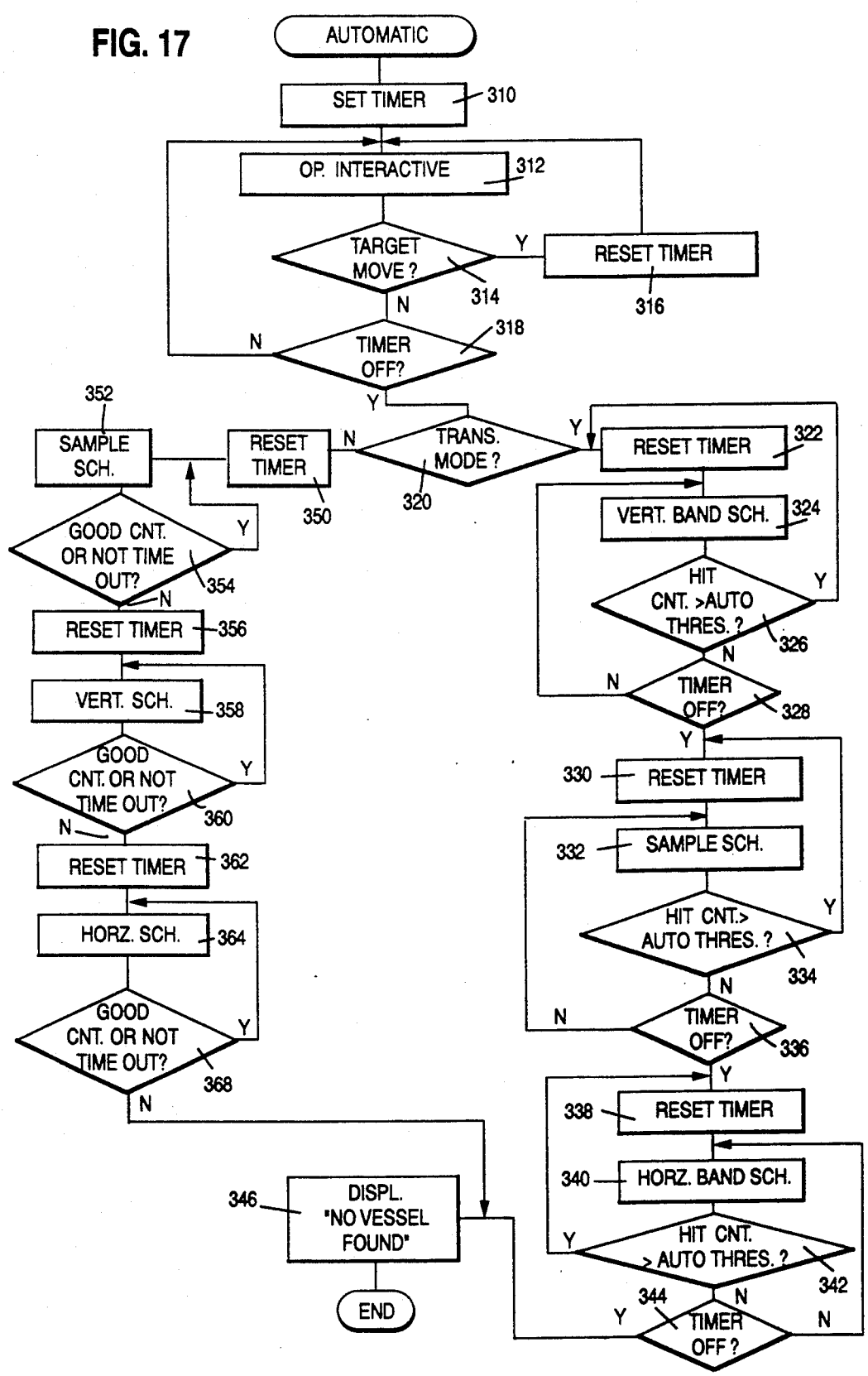

METHOD AND APPARATUS FOR DETECTING BLOOD VESSELS AND DISPLAYING AN ENHANCED VIDEO IMAGE FROM AN ULTRASOUND SCAN

BACKGROUND OF THE INVENTION

The present invention relates to a method and an apparatus for detecting blood vessels from video images generated by a B mode ultrasound scan of subcutaneous blood vessels and for displaying an enhanced video image highlighting the vascular walls on the video images obtained from the ultrasound scan.

Generally, B mode scans are utilized to view anatomical structures in a plane generally perpendicular to the surface of the skin. However, the typical ultrasound scan is presented to the physician or operator as a black and white image, i.e., a gray scale image. The quality of the image is poor, especially if the subcutaneous vascular structure is displayed in real time, because of the large amount of back scatter from both the vascular system and the surrounding tissue.

U.S. Pat. No. 4,812,622 to Pennypacker et al. discloses an infrared imager for viewing subcutaneous blood vessels. The system compensates for horizontal sweep of the NTSC video image to even the image background. The system also averages horizontal lines for vertical image uniformity. Further, the Pennypacker et al. system amplifies the video image to obtain a high contrast enhancement of the image. A logarithmic format is utilized in the system. U.S. Pat. No. 4,720,871 to Chambers discloses digital image convolution. U.S. Pat. No. 4,437,161 to Anderson discloses a medical imaging apparatus which obtains a video signal from an x-ray detector. A difference signal is obtained by subtracting a reference image signal from a second individual image signal. If the difference exceeds a threshold, a change image signal is generated. U.S. Pat. No. 4,802,002 to Plut et al. discloses a medical diagnostic television imaging system at the X-ray source, an image-intensifier tube and a video camera. Circuitry is provided for suppressing delivery of certain video images to the monitor in response to selection of one of the plurality of scan rates. U.S. Pat. No. 4,737,842 to Nagasaki discloses a color-emphasis circuit for color endoscope. The system modulates color signals, averages the color signals and detects hue differences between the modulated color signal and the modulated averaged signal. A hue difference changer is provided for widening the detected hue difference. U.S. Pat. No. 4,841,360 to Bergmeir discloses an apparatus for reproducing colored originals with an additional gray scale balance and/or color contrast adjustments. U.S. Pat. No. 4,742,388 to Cooper et al. discloses a color video endoscope system with an electronic color filtering. The endoscope senses sequential fields of red, green and blue light reflected from a patient. U.S. Pat. No. 4,831,437 to Nishioka et al. discloses a system with color balance adjusting mechanism. U.S. Pat. No. 4,805,016 to Kato discloses another endoscopic system.

U.S. Pat. No. 4,170,987 to Anselmo et al. discloses a medical diagnosis system sensing various wavelengths of light reflected from a patient. U.S. Pat. No. 4,751,643 to Lorensen et al. discloses a system for processing nuclear magnetic resonant signals. U.S. Pat. No. 4,754,332 to Bergquist discloses a device for presenting and selectively altering the brightness of a digitized image. U.S. Pat. No. 4,823,194 to Mishima et al. discloses a method for processing gray scale images.

U.S. Pat. No. 4,199,748 to Bacus discloses a system for identifying characteristics of red blood cells. U.S. Pat. No. 4,731,743 to Blancato discloses a system for analyzing hair styles. U.S. Pat. No. 4,812,909 to Yokobayashi et al. discloses a cell classification system.

One prior art system senses blood flow utilizing Doppler principles and a specially configured ultrasound scanner. Soundwaves from the ultrasound scanner are presented in a phased array and electronic circuitry connected to the scanner senses a Doppler shift in the return signals. This system is called a Quantum QAD-PV Angiodynography Imaging System sold by Quantum Medical Systems, Inc. of Issaquah, Wash. Blood flow through blood vessels is detected by the Doppler shift in the signals and the system color enhances the generally black and white or gray scale video image produced by the scanner. The blood flowing through the vessels is displayed in red whereas the background, that is the surrounding tissue, is displayed in black and white.

OBJECTS OF THE INVENTION

It is an object of the present invention to provide an electronic processing system which receives the sequential NTSC black and white video image from an ultrasound scanner, detects blood vessels represented in that video image and video highlights the vascular walls of those vessels.

It is another object of the present invention to utilize a series of electronic processing techniques to detect the vascular walls in the real time video image signal.

It is a further object of the present invention to detect the vascular walls and display those vascular walls in color as compared to the black and white background video image such that the vascular walls are color enhanced.

It is a further object of the present invention to electronically process a sequential plurality of video images and display enhanced video images all in real time.

SUMMARY OF THE INVENTION

The system for detecting blood vessels and displaying an enhanced video image from video images obtained from an ultrasound scanner includes, in one embodiment, a target filter which limits the area in the video image to a predetermined size and an edge detector which senses gradients in pixel values in that target area. The edge detector marks transitional pixels at gradients exceeding a certain level. The system also includes a monitor for displaying the video image obtained from the ultrasound scanner. The marked transitional pixels are displayed in a contrasting color compared to the concurrently displayed input video image. In one embodiment, the target filter detects motion by comparing moving image block target areas separated in both time and space, counting moving image blocks and further limiting the target area to areas having the highest number of moving image blocks. Accordingly, smaller target areas are processed with the edge detector. In another embodiment, the target filter includes a gross edge detector, a transitional pixel counter and further target filter which prioritizes the various initial target areas such that the target area having the highest number of marked pixels is selected as the area to be further processed by the edge detector. In both embodiments, the electronic processing occurs in real time. A method is disclosed for detecting blood vessels and displaying an enhanced video image from a plurality of video images obtained from an ultrasound scanner.

BRIEF DESCRIPTION OF THE DRAWINGS

Further objects and advantages of the present invention can be found in the detailed description of the preferred embodiments when taken in conjunction with the accompanying drawings in which:

FIG. 6 schematically illustrates the major hardware components of a system constructed in accordance with the principles of the present invention;

FIG. 7 graphically illustrates color enhancement of a gray scale signal;

FIG. 8 graphically illustrates horizontally weighted averaging of a pixel Pn, a convolution kernel for that pixel and motion detection of moving image block target area respectively centered about pixels Pn, Po, Pp;

FIGS. 9A and 9B are flow charts illustrating the principal steps in an operator interactive system;

FIG. 10 is a graphic illustration of the video image, initial target area and subsidiary target areas;

DETAILED DESCRIPTION OF THE PREFERRED EMBODIMENTS

The present invention relates to a method and apparatus for detecting subcutaneous blood vessels from sequential video images produced by an ultrasound scanner and displaying an enhanced video image, or a series of images, highlighting the vascular walls.

Ultrasound B mode scanning is relatively well-known and used in the medical community. The scanning head is placed on the skin of the patient near or above the anatomical item that the physician wishes to view. The scanning head emits ultrasonic waves which are reflected off the various tissues and other anatomical structures and the head further detects the return waves. The scanner includes signal processing circuitry which gathers this electronic information and displays the information in a video format on a monitor to the physician or operator. Some ultrasound scanners include a signal output port at which the electronic version of the video image obtained from the ultrasound scanner can be obtained. The signal at this output port is an NTSC formatted video signal consisting generally of a plurality of video frames, thirty frames per second, which can be further broken down into sixty fields per second where alternate horizontal scan video lines are present in each pair of consecutive fields.

The present invention is adapted to be electrically connected to the ultrasound scanner such that the invention receives as an input the sequential series of video images from the scanner.

Figure 1:
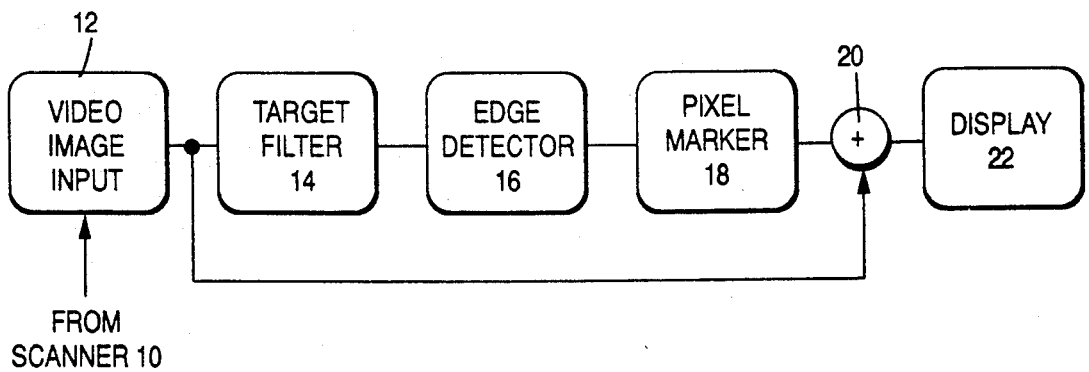
FIG. 1 schematically illustrates the major functional elements of the invention.
Figure 2:
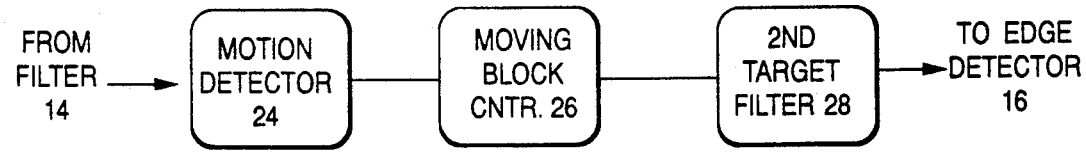
FIG. 2 schematically illustrates the functional elements of one type of target filter.
Figure 3A:
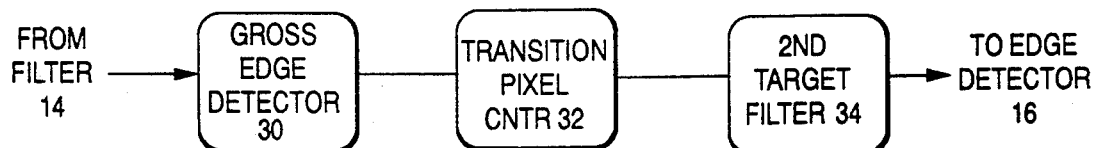
FIG. 3A schematically illustrates the functional elements of a second type of target filter.

FIGS. 1, 2 and 3A diagrammatically illustrate functional elements defining aspects of the present invention. The functional elements could be configured as hardware. FIG. 1 diagrammatically illustrates video image input 12 receiving the series of NTSC video images from scanner 10. Scanner 10 is the ultrasound scanner discussed above. Video image input 12 is connected to a target filter 14. The target filter defines and narrows the area in the video image such that the area is electronically processed. The system processes video image data in the target areas and operates on the series of images substantially in real time. For example, assume that the video image is a 512 pixel square matrix that consists of 512 pixels wide and 512 horizontal lines. The target filter is utilized to electronically designate the most likely area or areas in each video image where the blood vessel may be found. For example, if an extremely fast microprocessor (e.g., 80286, 80386 or higher) and associated hardware were used to implement the present invention, the target area may be 70 to 80 percent of the video image. Electronic processing of this target area is appropriate because the subcutaneous blood vessels sought to be detected are normally not found in the upper and lower 10% of the video image. Therefore, target filter 14, in its broadest form, simply limits the range of electronic processing area on the video image to an area where the blood vessels will most likely be found. Of course, if the vessels were close to the skin surface, the target area could be moved to include the top 30% of the video image. On the other hand, if a slower microprocessor (e.g., 8088) were utilized to electronically process the video image, target filter 14 would select a smaller percentage of the input video image from scanner 10 for further electronic processing.

Figure 4:
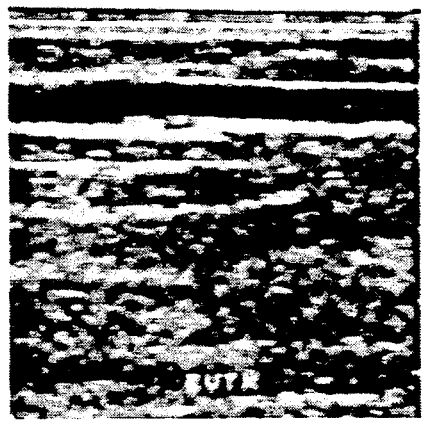
FIG. 4 is a photographic reproduction showing the grain and background noise of a video image from a B mode ultrasound scan showing the lateral view of a vein.

Connected to the output of target filter 14 is an edge detector 16. Essentially, edge detector 16 senses gradients in pixel values in the portion of the video image passing through target filter 14 and determines whether those gradients exceed a certain level. It is known in the art that each video image frame consists of a matrix of pixels and each pixel has a certain value associated with it, that value being essentially a brightness or intensity of the video image at that particular horizontal line and vertical time-based position. Generally, the output from the B mode ultrasound scanner is a black and white video picture in an NTSC format. Therefore, each pixel has associated with it a particular gray scale value. The gray scale value could range from 0 through 256. FIG. 4 photographically illustrates the high degree of background noise or grain in the video input signal. Running from left to right horizontally across FIG. 4 is shown a vein.

Edge detector 16 (FIG. 1) is configured to sense gradients in pixel values and to sense the presence of vascular walls. Various algorithms for sensing these gradients are discussed later. After identifying gradients in the pixel values, pixel marker 18, connected to the output of edge detector 16, marks transitional pixels at predetermined gradients representing vascular walls about a lumen of the blood vessel. For example, the edge detector may compute the second differential between each substantially vertically aligned pixel value. This procedure senses vertical gradients in pixel values. If the second differential exceeds a certain value, for example 2, this excessive pixel gradient could represent a vascular wall. Pixel marker 18 then identifies the pixel associated with this excessive gradient and since this pixel represents the vascular wall, pixel marker 18 assigns a color, for example, red to that pixel. Essentially, pixel marker 18 writes a prescribed pixel value into the signal storage location of the transitional pixel in the particular video frame image. The output of pixel marker 18 is coupled to a summer 20 which sums the marked transitional pixel with the video image that is obtained as an input from ultrasound scanner 10. By adding the specially marked pixel to the video image from the scanner, the marked pixel value overwrites the original pixel value in the video image. Display 22, coupled to the summer, concurrently displays the input video image and all of the marked transitional pixels.

Although the input video image signal from ultrasound scanner 10 is in a black and white or gray scale format, it is helpful to video highlight the marked pixels by introducing a contrasting color into that input video image. By highlighting the vascular walls with the color red, this video highlighting sharply contrasts the vascular walls as compared to the underlying or background gray scale video image. Accordingly, the physician or operator utilizing the system could easily identify the vascular walls surrounding the lumen of a blood vessel. Since the ultrasound B mode scanner views the blood vessel through a cross-sectional plane, only the upper and lower portions of the blood vessel are shown in color on the monitor or display 22 if a lateral view of the vessel is scanned. However, if a transverse view is shown (FIG. 5), that is by turning the ultrasound scanning head 90 degrees on the surface of the skin, the scanner takes a cross-section transversely through the blood vessel rather than longitudinally along the blood vessel. The resulting input video image ma look similar to the photograph in FIG. 5.

Once the electronic processor has identified the upper and lower vascular walls in a lateral scan, the entire vein or artery could be highlighted by an appropriate algorithm. However, by highlighting primarily the vascular walls, the physician or operator receives more information regarding the ultrasound scan since the contrasting color does not block out, mask or detract from the remaining portions of the video image. Of course, rather than displaying the marked transitional pixels in a contrasting color, the display could illustrate those pixels by unique indicia such as dots, arrows, dashes, etc. as long as the transitional pixels were visually differentiated from the background input video image. Accordingly, the phrase "contrasting color compared to the concurrently displayed video image" refers to any type of display that significantly visually distinguishes the background video image input from the ultrasound scanner from the marked transitional pixels identified by edge detector 16.

FIGS. 2 and 3A diagrammatically illustrate further refinements to target filter 14. Since processing time is important, the input video image usually is screened and only a certain portion is processed. For example, it may not be necessary to process a peripheral 5–10% boundary about the input video image for a vascular structure. In this sense, target filter 14 is utilized in a limited capacity when used in conjunction with the functional devices illustrated in FIG. 2. A motion detector 24 has its input coupled to target filter 14. The specific configuration of the motion detector will be discussed later. The motion detector essentially detects moving image blocks within pre-established portions of the sequential plurality of input video images. The motion detector correlates in time and space blocks of averaged pixels. For example, if there is an anatomical structure, i.e., blood, moving through the ultrasound scanning region, the visually represented segments of the blood should be electronically represented essentially the same as the segments or image blocks move across the viewing field. Therefore, the motion detector first identifies a block of pixels in one frame. The block is a predetermined number and configuration of pixels within a larger target area or preestablished portion of a first input video image or first video frame. The motion detector then compares the value of that block of pixels with the value of a second block of pixels obtained from either a single subsequent video frame image or a series of subsequent video frame images. Further, the block value from the subsequent frame or frames is not physically located at the same location of the image as the first block from the first sequential image because it is assumed that the block has moved. Therefore, the block value computed for the subsequent video frame encompasses a different region or space on the frame. Accordingly, the motion detector correlates in time and space blocks of pixels. If the correlation reveals an identical or substantially identical image block value, one that is similar within a predetermined range, then motion has been detected in this sequential plurality of input video images. When viewing subcutaneous regions in a patient in the vicinity of blood vessels, most likely the only item moving relatively fast through the images will be the blood through the blood vessels. By establishing and carefully defining the spatial differentiation between image blocks and the time differentiation between the two image blocks, motion detector 24 can be set to detect blood flow.

After identifying the moving image blocks within the preestablished portions of the input video images, motion detector 24 passes this identification information to moving block counter 26. Moving block counter 26 counts the instances within the preestablished portion of the input video image and passes this block count to a second target filter 28. For example, assume that four target regions were identified and passed through target filter 14 to motion detector 24. Out of those four target areas, target area 1A was found to contain 50 instances of moving image blocks, target 2A had 37 blocks, target 3A had 4 blocks and target 5A had no blocks. The second target filter 28 prioritizes or orders these multiple target areas such that the highest order target area 1A has the greatest number of identified moving blocks therein. The second ordered target area 2A has the second largest number of moving blocks, etc. The output of second target filter 28 is passed to edge detector 16. Therefore, edge detector 16 receives a smaller target area which is electronically processed to detect vascular walls. By reducing the size of the target area, more complex electronic calculations can be conducted in the target area to detect vascular walls. Because of the high degree of noise in the input video image (see for example photographs in FIGS. 4 and 5), this process of narrowing and prioritizing or ordering the target areas can be iterative in nature.

FIG. 3A diagrammatically illustrates another method and apparatus for narrowing the target area such that edge detector 16 can utilize higher order electronic processing techniques. Gross edge detector 30 obtains an input from the first target filter 14. Gross edge detector 30 may look for the second differential in the pixel gradient and determine whether that second differential exceeds a predetermined value. In contrast, edge detector 16 (FIG. 1) may utilize a convolution routine which requires a much longer processing time when compared with processing the video images vertically with differential equations. The output of gross edge detector 30 therefore identifies pixels whose gradients exceed a certain threshold. Transition pixel counter 32 counts the number of those excessive gradients found in the targets. Again, rather than electronically processing 80% of the video input image as a whole, that 80% image may be segmented into, for example, quadrants that are sub-target areas. Transition pixel counter 32 counts the number of transition pixels identified in each quadrant within the total area processed by gross detector 30. Second target filter 34 is coupled to the output of transition pixel counter 32. The second target filter 34 orders these various sub-targets and places the highest order target or quadrant, having the greatest number of transition pixels identified by pixel counter 32, on the top of a stack. If the transitional pixel count exceeds a certain value, second target filter 34 may pass the stacked or ordered sub-target area to edge detector 13. If however the transitional pixel count does not exceed a certain predetermined threshold value, second target filter 34 feeds the stack of sub-targets to a feedback loop 36 which further segments the sub-target areas. For example, assume that 80% of a video image was first identified as the first target area by filter 14. The target is segmented into quadrants and each quadrant is a sub-target area.

If the transition pixel count does not reach a certain value in at least one sub-target area, feedback loop 36 takes the first two ordered sub-target areas, segments those sub-target areas into quadrants, and orders those sub-sub-target areas by transitional pixel counts. Feedback loop 36 could also change the gross edge detector 30 algorithm from a second differential, individual pixel value algorithm to a second differential, horizontally weighted average pixel value algorithm. The output of feedback loop 36 is fed to target filter 14 such that the gross edge detector operates on eight sub-sub-target areas using a second differential, horizontally weighted average pixel values. In this situation, feedback loop 36 changes the threshold in the second target filter because of the number of transitional pixels counted by counter 32 maybe less than the transitional pixels found in the quadrant or sub-target area.

In any event, this iterative process continues until a target area is identified as being the most probable for detecting vascular walls. Several embodiments are discussed hereinafter illustrating these principles. However, the embodiments are exemplary since various features of each embodiment could be combined in a number of ways to accomplish the ultimate result of identifying and colorizing vascular walls. An important aspect of the invention is that the vascular walls, or at least a portion of the vascular walls, be electronically identified and video highlighted in substantially real time. Of course, electronic processing is dependent upon the speed of the microprocessor, the quality of the memory utilized in conjunction with the microprocessor and the input and output handling capabilities of the processor. Since the processing speeds are continually increasing, the system described herein may be simplified by utilizing an extremely fast microprocessor. If a slow microprocessor is utilized, the target operated on by the edge detector machine must be reduced in order to display the enhanced video in substantially real time.

Substantially real time, as used herein, may encompass displaying marked transitional pixels that were identified ten and as many as twenty frames earlier but are in the, for example, twentieth frame. Although the particular location on the screen would not be a precise accurate representation of the vascular wall, the actual physical distance between the illustrated marked transitional pixel and the actual pixel showing the vascular wall would be minimal. Further, as discussed later, the operator or physician can alter the various parameters and thereby eliminate or reduce the frame delay and hence improve the accuracy of the system.

Figure 3B:
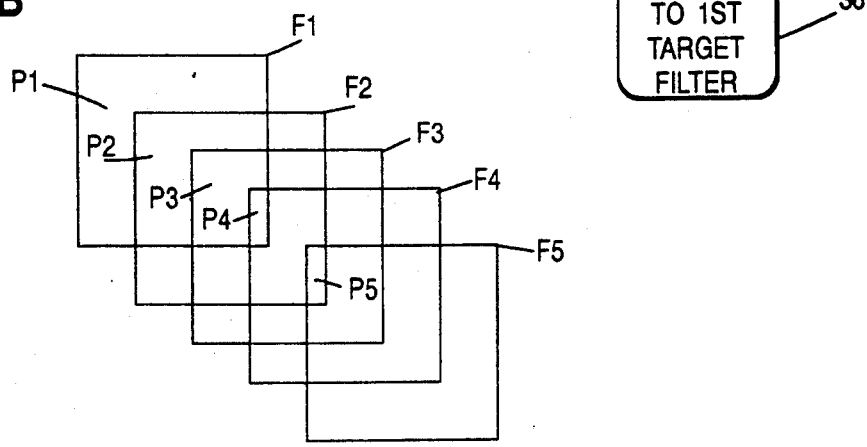
FIG. 3B diagrammatically illustrates processing and marking the sequential video images in real time.

The processing is done substantially in real time. The NTSC gray scale video signal from the ultrasound scan is obtained from the scanner, a portion of that frame signal is processed, transitional pixels are marked, and the video frame is displayed generally concurrently with the contrasting color marked pixel. FIG. 3B diagrammatically illustrates processing and marking in substantially real time. Frames F1, F2, F3, F4 and F5 are a sequential plurality of gray scale scan video images. Pixels P1, P2, P3, P4 and P5 are pixels at the same location in correspondingly numbered frames. Assume that these pixels also represent a vascular wall. However, due to the processing time and the hardware constraints, assume that the processing time for identifying transitional pixel P1 in frame F1 is longer than the time period of two video frames. This processing limitation could be due to the slow speed of the microprocessor and associated computer hardware, the high degree of background noise in the input video image which requires a further narrowing of the target area, and the increasing complexity of the edge detection routines in those narrower areas. Alternatively, the operator or physician utilizing the system may wish to have the system be extremely accurate in identifying the vascular walls. As discussed later, the physician or operator can set certain parameters, thresholds, hit counts, etc. which cause the system to identify fewer transitional pixels and cause the system to have a greater accuracy in identifying the vascular walls. For whatever reason, assume that the system cannot identify and mark pixel P1 in frame F1 until the system displays video input frame F3. Assuming that the video input frame F1 is the first frame which the system is operating on, transitional pixel P1 would not be identified until frame F3 is being displayed. Pixel P1 would be assigned or marked a red color and pixel P3 in frame F3 would be overwritten in red. The electronic processing system could then "grab" video frame image F3 and process it and identify pixel P3 as a transitional pixel at a vascular wall. In the meantime, display 22 in combination with summer 20, will overwrite gray scale pixel P3 in frame F3 with color red because of the identified transitional pixel P1 in frame F1. By frame F5, pixel P3 has been identified as transitional pixel and the color red is assigned to pixel P5. Accordingly, edge detector 16 marks sequential transitional pixels, and in FIG. 3B, pixel P1 overwrites the intermediate gray scale pixels P3 and P4 in the sequential plurality of input video images (F1, F2, F3, F4 and F5) with the marked sequential transitional pixels. Sequential colorized or marked pixels P1 and P3 overwrite gray scale, original pixels P3, P4 and P5 in frames F3, F4 and F5. As used herein, the term "concurrently displaying" refers to displaying both the input video images from the ultrasound scanner and the marked transitional pixels such that the operator or physician can readily identify the vascular wall on the display monitor.

FIG. 6 diagrammatically illustrates a current embodiment of the present invention and shows the principal hardware components thereof. An ultrasound scanning head 40 is utilized to scan a patient with B mode scans. Signal conditioner 42 is part of the ultrasound scanning device. Signal conditioner 42 produces generally an NTSC gray scale video signal. Of course, a PAL video signal could be utilized or other standard video signal. After understanding the principles of the present invention, a person of ordinary skill in the art could easily convert the invention to operate on PAL or other type of video format signals. The video signal on line 44 is applied to an image processor board 48. This image processor board is currently an Oculus OC300 Image Processing Board from Coreco, Inc. of St. Laurent, Canada. As will be explained later, this image processing board and the operations conducted therein could be replaced by software routines stored in the memory associated with microprocessor 66. Image processing board 48 is mounted in an IBM AT personal computer or an AT compatible computer. The processing board includes an analog to digital (A/D) converter 50, a double input look-up table (DILUT) 52, a frame memory 54, a look-up table (LUT) 56, a digital to analog converter (D/A) 58, and a look-up table selector (LUT SEL.) 60. The look-up table selector 60 is part of a feedback loop.

To explain a simple operation of the image processing board, reference will be made to FIG. 7 which diagrammatically illustrates a color enhancement chart for various gray scale values. The intensity or brightness of the color is shown on the vertical axis and the corresponding gray scale value from 0 to 256 is shown on the horizontal axis. From gray scale values from 0 to 86, the color blue (B) is substituted at various intensity levels. Between the gray scale values of 86-172, the color red is added to the full intensity blue and, in that region, a color monitor 62 (FIG. 6) displays those pixel values as shades of green. For gray scale values between 172 and 256, the blue is removed from the signal and red (solid line in FIG. 7) is maintained at its highest intensity such that at gray scale value 256, the pixel value is completely red. Dilut 52 is configured as a simple look-up table that converts a gray scale pixel value, e.g., 256, to a color, e.g., red. Only pixel values equal to 256 will be colorized red.

FIG. 8 diagrammatically and graphically illustrates three aspects of the invention. On the horizontal axis, distance is shown. Therefore, pixel Pn is horizontally spaced on the frame image away from pixel Po. Pixel Pp is spaced even further from pixel Pn. Those distances being respectively X1, X2 and X3. On the vertical axis time is shown. Therefore, in a time based comparison, the 10×3 group of pixels about pixel Pn is processed at a different time and is in a video frame (e.g., F1 in FIG. 3B) as compared with the 10×3 group of pixels about pixel Pp (F2). The time corresponding to pixels Pn, Po, Pp is respectively t1, t2 and t3. The three things that FIG. 8 illustrates is motion detection of image target blocks, both spatially and in time; the horizontal weighted average of a particular pixel with neighboring pixels; and a convolution kernel for a particular pixel.

To explain another simple operation of the image processing board, horizontal weighted averaging of pixel Pn will be discussed. In some instances, the physician or operator will be scanning the blood vessels along their longitudinal extent (a lateral scan per FIG. 4) and the vascular walls initially illustrated by gray scale images will run somewhat horizontally acros the video display. It has been discovered that the lumen of the blood vessels is usually represented by very dark gray scale values as compared with the surrounding tissue. Further, the vascular walls are sometimes, but not always, electronically represented in lighter shades on the gray scale. See the photograph in FIG. 4. Therefore, by vertically detecting edges on a single video image, the vascular wall is detected. In order to further emphasize that a particular pixel represents a transition between non-vascular tissue and blood in the vessels, each pixel is averaged with a plurality of neighboring pixels to obtain a horizontal weighted average. In FIG. 8, pixel Pn is averaged with neighboring pixels such that the averaged block is ten pixels wide and three pixels high (10×3). Similar averaging is done for the pixel Pn-1 immediately to the left of the pixel Pn, and all the other pixels in the particularly defined target area. The horizontally weighted average of the 10×3 goup about pixel Pn replaces the original gray scale value of pixel Pn.

The image processor 48 can be configured to obtain a horizontally weighted average of the pixels within a certain target area of the video input image obtain the difference between substantially vertically aligned pixels so averaged, and if the difference between the vertically adjacent pixel values exceed a certain threshold, that indicates that the pixels are very near or on the electronically represented vascular wall. The edge detection routine in this embodiment obtains a horizontally weighted average of the pixels, obtains the difference between vertically aligned pixel values and determines whether the difference exceeds a threshold. If so, one or both of the vertically adjacent pixels are identified as transitional pixels. A "Color mark" is assigned to the transitional pixels. For example, all transitional pixels may be assigned a gray scale 256 value. Later, the 256 value is recognized as red. Frame memory 54 holds two frames of 512×512 pixels wherein each pixel occupies one byte of memory, that is eight bits representing a gray scale value between 0 and 257. Importantly, frame memory 57 can be split to hold four frames of video images by reducing the sensitivity of the gray scale from 257 values to 64 values. This is an important processing technique because the human eye can only differentiate approximately 64 values of gray (black and white), and so frame memory 54 can be configured to hold four frames rather than two. The system can process additional data within that four-frame time span. Look-up table selector 60 is software programmable, therefore the selector is attached to system bus 64 as is microprocessor 66, processor memory 68, and input-/output device 70. The system bus 64 is also connected to the dual input look-up table 52 and the frame memory 54.

In the simple operation identified above, look-up table selector 60 is set to obtain a horizontally weighted average of pixel Pn and to substitute that horizontally weighted average value for the original pixel value Pn. Microprocessor 66 then operates on horizontally weighted averages of the pixels in the specific frame or target area. Microprocessor 66 takes the difference between each substantially vertically aligned pixel and determines whether that difference exceeds a certain threshold value on a pixel by pixel basis. If an excessive difference is detected, microprocessor 66 marks a particular pixel frame location in frame memory 54 with, for example, a "red color" value of 256. Look-up table 56 is programmed such that a gray scale value of 256 is assigned the color red. Therefore, since frame memory 54 is changed for that particular pixel location, that pixel is marked by a contrasting color and color monitor 62 displays that colorized pixel signal concurrently with the original gray scale video image.

The system illustrated in FIG. 6 also includes an operator control 72 which consists of the customary keyboard, display monitor if necessary, and other types of electronic input/output devices.

The image processing board 48 can be replaced by software routines stored in memory 68 which are executed by microprocessor 66. In such a case, the NTSC video image signals on line 44 are fed directly into input/output device 70. In that I/O device, an A/D converter (similar to converter 50) is utilized to digitize the analog input signal. Microprocessor 66 executes various electronic processing routines on the input video frame signal in order to determine the presence of vascular walls. The benefit of using image processing board 48 is that the board provides additional memory, designated look-up tables and a software controlled look-up selector 60 that can be controlled or altered by microprocessor 66. Accordingly, the system includes a pixel averager in addition to an edge detector. The pixel averager averages pixel values over a predetermined horizontal range (in FIG. 8, a 10 pixel range) and assigns discrete average pixel values to each pixel in the target area being processed. Of course, the horizontal weighted average can be changed by altering the width or the height of the block to be averaged.

The system can be programmed to detect differences, differentials and convolutions. First, second and third differentials can be obtained for substantially vertically aligned adjacent pixels or vertically aligned or adjacent horizontally averaged group of pixels. These differences and differentials are compared to threshold values and if the differences or differentials exceed a certain value, the pixels associated with the processed pixel value are assigned or marked in a contrasting color such as red. Presently, since the lumen of the blood vessel appears dark in the video signal, the edge detection routine utilizes the second or third differential between horizontally weighted average pixel values. If the second differential between substantially vertically aligned averaged pixel values exceeds a pre-set threshold value, that pixel is marked as a blood vessel wall pixel, i.e. transitional.

The edge detection routine could also be a convolution of a predetermined number of neighboring pixels about pixel Pn. Convolution routines are well-known and are similar in some respects to horizontally weighted averaging combined with obtaining a differential of the specific pixel Pn at the "center" of the convolution kernel. The convolution kernel can be designated by the 10×3 pixel block shown in FIG. 8 about pixel Pn or can be something different. The Oculus image processing board convolutes the pixel values based on a 3×3 pixel block during an eight frame time span. Convolution in image processing essentially changes the gray scale value into a spatial frequency value. Then, microprocessor 66 identifies high frequencies and assigns color to pixels exceeding a predetermined value.

A currently favored convolution routine consists of determining the difference between the average pixel value in the top row of the pixel block (10×3) and the average pixel value in the bottom row of that block.

As stated earlier, FIG. 8 also shows the motion detection. Pixel Pn is averaged with a 10×3 block, ten pixels horizontally and three pixels vertically. The horizontally weighted average value is assigned to pixel Pn. In order to determine whether that 10×3 pixel block is a moving image block, the next frame is analyzed. Pixel Po is present in the next frame that is received at time t2 compared to time t1 of the previous frame. Pixel Po is also X2-X1 distant from pixel Pn. Both image blocks are correlated in time and in space. Therefore, with respect to the spatial relationship, the image block centered about pixel Po is shifted two pixels to the right from the image block about pixel Pn. Pixel Pn is at distance X1 whereas Po is at distance X2. There is an overlap between the Pn and Po image blocks because some type of correlation between each successive image block should be obtained. If the distance between successive image blocks is too great, no correlation will be found. If the distance is too small, there will be too much correlation. The correlation is simply the difference between the horizontally weighted average Pn and the horizontally weighted average Po. If the difference is 0, then there is a high probability that the image block initially found in the 10×3 block about Pn is the same as the 10×3 image block about pixel Po. Since Pn is captured at time t1 and Po at time t2, the correlation is also a time based comparison. It would be relatively unusual for the dynamic video image to have image block values which are equal over a prescribed time and distance unless the scanned image includes moving blood. Of course, the time span between t1 and t2 may be several frames or be separated up to 20 or 30 frames. The time span in the time based comparison can be set by the operator or physician as discussed later. Likewise, the distance between the moving image blocks is also based upon the speed of blood flow through the vessel. For example, if slow moving fluids in the vessels are analyzed and the quality of the input video images is very good, image blocks Pn and Pp rather than Po are compared. Of course, there is a higher probability of less correlation between image block Pn and Pp because there is only a 5×3 spatial overlap between these two image blocks.

Figure 9B:
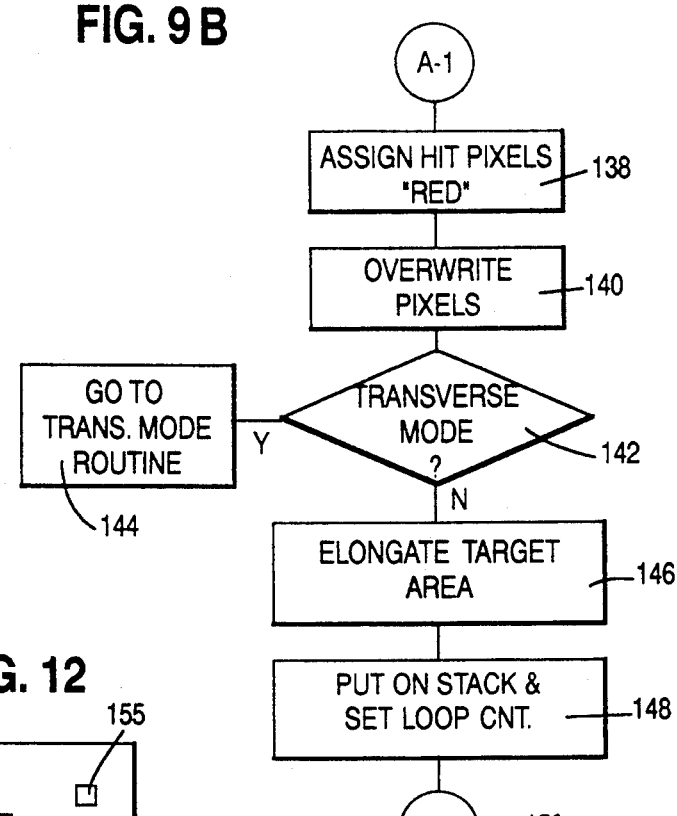

FIG. 9 illustrates a flow chart showing the chief steps in a user interactive system for detecting vascular walls from video images obtained from an ultrasound scan. Step 110 initializes the system. Step 112 displays the target area for the operator.

FIG. 10 diagrammatically illustrates a display monitor screen 101 or image frame and an initial target area 103. The operator or physician can electronically move initial target area 103 about screen 101 in step 114. For example, the physician may initially view an ultrasound video image similar to that shown in FIG. 4. The initial target area 103 is set at 50 pixels square in each direction. Since the operator or physician can visually identify the most probable area for the blood vessel detection simply by viewing the screen, the operator can move initial target area 103 about the screen or the video frame image, thereby assisting the system and limiting the electronic processing to a predetermined area in the video input image. In step 116, the system informs the operator or physician that the edge detection or processing is occurring.

In step 118, initial target area 103 is processed either utilizing an edge detection routine or a motion detection routine. If an edge detection routine is utilized, a first or second vertically oriented differential is calculated after obtaining a horizontal weighted average for all the pixels within initial target area 103. Alternatively, initial target area 103 may be analyzed on the basis of motion detection.

Decision step 120 determines whether the operator has moved the target. If the operator has moved the target, the routine returns to step 116 to display "processing" and then reprocesses electronic data in the new target area. Of course, in order to accommodate the operator moving target area 103, operator control 72 (FIG. 6) must include some type of cursor control such as a mouse or horizontal/vertical arrow controls. If the target has not moved during processing, the no branch is taken from decision step 120 to step 122. In step 122, initial target area 103 is subdivided into segments which in the illustrated embodiment are quadrants, one of which is quadrant or sub-target 105. If a gross edge detection routine was utilized in step 118, the number of pixel gradients exceeding an established threshold are counted on a per quadrant target basis. The sub-target quadrant area having the greatest number of excessive gradients detected therein is placed first on a push down memory stack (last in, first out). Therefore, the sub-target quadrants are ordered based upon the number of detections. Step 124 sets a loop count (loop cnt.) equal to the number of target areas on the stack. In the illustrated embodiment, there are four sub-target areas on the stack, therefore the loop count is set at 4.

Decision step 126 determines whether, after incrementing a loop counter (loop cntr. initially set at 0), the loop counter is greater than the loop count. If the loop counter is greater, that is an indication that the detailed or fine edge detection routine has operated on all the sub-target areas in the stack and that the loop should be exited. This conforms to a yes branch taken from decision step 126 which enters step 128. Step 128 displays a message "no vessel found" to the operator indicating that after sufficiently processing the target area 103, no blood vessel was found. Step 130 re-initializes the system and returns the program to display target area step 112.

If the fine edge detection routine has not operated on all of the sub-targets in the stack per decision step 126, then the no branch is taken from the decision step. In step 132, the system convolutes the first target area, sub-target area 105, on the stack. Convolution is a fine edge detection routine which requires more processing time than the gross edge detection routine. In step 133, the system counts the number of hits or the number of pixel gradients exceeding a higher gradient threshold. This gradient threshold is higher than the initial threshold utilized by the gross edge detection routine. In decision step 134, a decision is made as to whether the hit count exceeds a count threshold. If the hit count in the highest ordered sub-target area 105 does not exceed a count threshold, the no branch is taken and in step 136, the next highest ordered sub-target is taken from the stack and processed. After step 136, decision step 126 is encountered which increments the loop counter and makes the determination whether the fine edge detection routine has operated on all of the sub-target areas in the stack. The routine processes all the sub-targets utilizing the fine edge detection routine (convolution) until either all the sub-targets are processed or the hit count in one sub-target exceeds the count threshold. Although a convolution edge detection routine is used in step 132, other edge detection routines could be utilized therein. For example, Fourier transforms could be utilized to detect high frequency peaks in the pixel values.

If the hit count in decision step 134 exceeds a count threshold, the yes branch is taken and in step 136, the count zzthreshold is set equal to the hit count found in that sub-target area. In step 138, the transitional pixels identified by the convolution in step 132, that is the pixels having the excessively gradient between vertically adjacent or vertically aligned pixels, are assigned the color value red. In step 140 the system overwrites the transitional pixel locations in the video frame with the red color value. In decision step 142, the system determines whether the operator or physician has selected a transverse mode. The transverse mode is selected by the operator if the blood vessel scan is similar to that shown in the photograph of FIG. 5. If the transverse mode has been selected by the operator, the decision step 142 takes the yes branch and step 144 takes the main system to the transverse mode routine that is discussed later in conjunction with FIG. 16. If the operator has not selected the transverse mode, the no branch is taken and in step 146 the system horizontally elongates the target area. After elongating or further changing the sub-target area, the system in step 148 places the changed sub-target area on the top of the stack and sets the loop counter equal to the larger stack value.

In step 150 the system jumps to jump point A-2 immediately prior to the detailed or fine edge detection step (convolute target number one) step 132.

As another example, assume that rather than elongate target area step 146, the system further segmented sub-target area 105 into quadrants to obtain sub-sub-target areas. The hits in sub-sub-target area, e.g., area 107, are counted and the sub-sub-target area with the highest hit count is the highest ordered sub-sub-target area on the stack. The stack then consists of sub-sub-target area 1 (area 107), sub-sub-target area 2, sub-sub-target area 3, sub-sub-target area 4, sub-target 105 (FIG. 10), sub-target area 2, sub-target 3 and sub-target area 4. In step 148, the sub-sub-target area 107 is placed first on the stack and the loop count is set at 8. The program then jumps to jump point A-2 immediately preceding edge detection/convolution step 132. Sub-sub-target area 107 is convoluted and the gradients exceeding a pre-established value are counted in step 133. Decision step 134 determines whether the hit count in sub-sub-target area 107 exceeds the count threshold set by the sub-target area 105. Assuming that the blood vessel is in the double cross-hatched area 107 in FIG. 10, the sub-sub-target area hit count should be higher than the sub-target area 105 hit count. Therefore, the yes branch is taken from decision step 134. The count threshold is set equal to the new and higher hit count from the sub-sub-target area. Red is assigned to those transitional pixel locations in the frame in step 138. The red pixels overwrite the original values in step 140. The transverse mode decision is encountered in step 142 and the target area is elongated or further changed in step 146.

Accordingly, the target area change routine in step 146 could first diminish the initial target area to a certain point and then begin horizontally elongating that target area. The degree to which the elongation occurs depends upon the reset hit count threshold and the programmed expansion of the target area. When viewing the lateral vein shown in FIG. 4, a preferred embodiment of the invention electronically identifies a single vascular wall by fine edge detection in a certain narrow target area and then elongates the target area. Accordingly, the physician or operator has a better sense of where the entire blood vessel is. It may not be essential to highlight all of the blood vessel if the majority of the blood vessel wall is colorized. By establishing hit count thresholds and iteratively contracting or making smaller the target area and then when the hit count exceeds a certain threshold gradually elongating the target area horizontally, the operator first obtains a sense of where the best scan vein portion is located. After the vascular walls are video highlighted in that narrow portion, the system automatically expands that target area into the neighboring vertical region to encompass the opposite vascular wall and additional vascular wall portions to the left and the right of the particular target area initially processed.

Accordingly, dependent upon the hardware used in the system (contrast the speed of an 8086 microprocessor with the speed of a 386 microprocessor) the degree of background noise or nonessential signals obtained from the ultrasound scanner and the desired sensitivity required by the operator or physician utilizing the system, the system first defines a target area processes that area to determine whether there are blood vessels in the area. This initial processing could be the motion detection routine discussed earlier or a gross edge detection routine utilizing a first, second or third, vertically oriented differentials of horizontally weighted pixel averages and comparing those differentials against a relatively low threshold gradient level. The system then further limits the target area to a sub-target area which can be extensively processed by the convolution routine or higher forms of edge detection such as Fourier transforms, etc.

Most importantly, the marking of transitional pixels with the color red or other contrasting color is done in substantially real time such that the operator seeing the ultrascan video image also sees marked transitional pixels that have been marked by the system soon after the video frame is input into the system. That time must be within one or two seconds given the dynamic nature of the item being scanned. If the physician or operator wants a very sensitive system, the operator holds the ultrasound scanner steady on a patient moves the target area around the video screen such that the system processes, for example, a one-sixteenth sub-sub-target area within that user-defined target area. The operator or physician may consider this technique acceptable if the operator wanted precise identification of vascular walls. However, if the operator wanted to identify vessels and was not so concerned with the accuracy or false positives that might be generated by setting the gradient thresholds at low levels, the operator can choose to sacrifice accuracy of the system in favor of processing speed.

Figure 11:
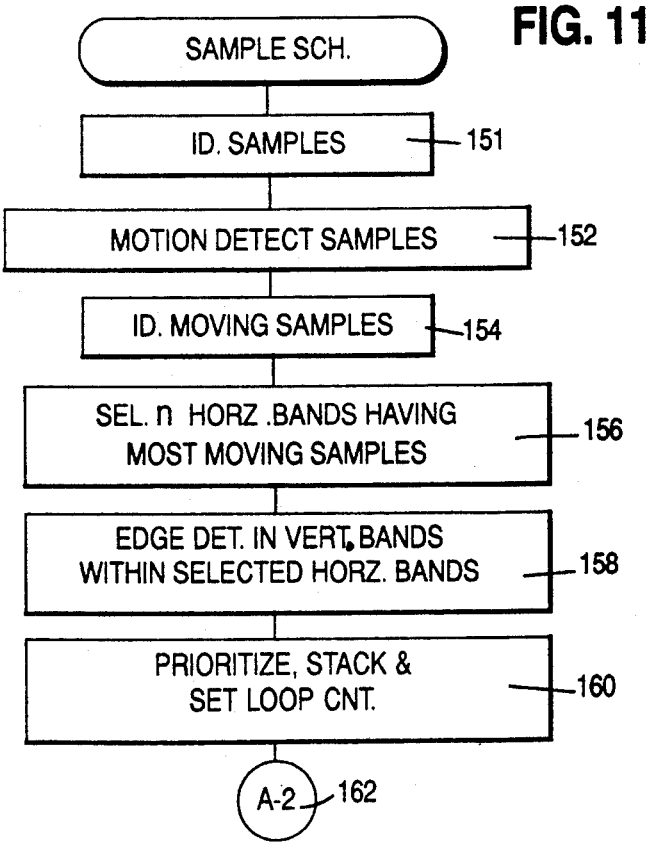
FIG. 11 is a flow chart showing the principal steps of a sample search routine.

FIG. 11 illustrates a flow chart of a sample search and the principal steps thereof. Again the chief function of the present system is to identify in an acceptable time period the most probable location of the blood vessel, define a reasonable target area in that probable location, extensively process that probable location and determine whether blood vessel walls are present in that location. If the processing does not obtain a reasonable hit count in that identified narrow target area, the system then operates on other target areas stacked or identified as progressively less probable. The operator-interactive system discussed with respect of FIG. 9 enables the use to view the ultrasound video images and then place the initial target area over the most probable location. Also, as described later, the user can increase or decrease the size of initial target area and therefore increase the the system,s response time.

Figure 12:
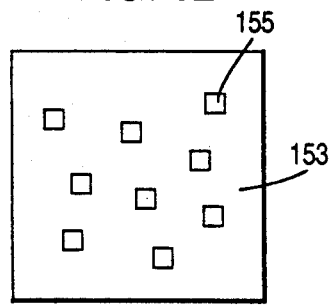
FIG. 12 is a graphic illustration of the video image with a plurality of sample areas or target areas illustrated thereon.

FIG. 11 shows a method of quickly identifying the most probable region in the input video image for the blood vessels. In step 151, sample regions are identified in the input video image. FIG. 12 graphically illustrates a video image 153 with several sample regions shown thereon, one of which is sample region 155. For example, 1000 samples of $10 \times 3$ pixel blocks can be utilized. In step 152, the sample search routine detects motion in image block target 155. The motion detection encompasses selecting and averaging a $10 \times 3$ image block, e.g., around pixel Pn in FIG. 8, and comparing that potentially moving image block with the $10 \times 3$ image block target slightly moved spatially from target 155 in a subsequent video frame, e.g., pixel Pp in FIG. 8. Step 154 identifies moving samples by correlating in time and space blocks of pixels. If the difference between two image block targets is 0 or the difference is less than a pre-set level, the sample is identified as a moving image sample. In step 156, the program selects n horizontal bands having the most moving samples. To accomplish this, screen 153 is subdivided into horizontal bands. For example, each band could be ten video scan lines high for a total of approximately fifty horizontal bands corresponding to 500 lines in the video frame image. Step 156 counts the number of moving image blocks per band and then prioritizes or orders those horizontal bands per number of hits or identified moving image blocks. The highest order horizontal band corresponds to the band with the greatest number of moving image blocks.

In step 158, an edge detection routine is executed. The horizontal bands are further subdivided into a plurality of vertical bands. For example, a horizontal band may be divided into six segments. Within each segment, the program conducts a vertical edge detection routine in a three pixel wide vertical band and detects vertical edge gradients at, e.g., six evenly spaced vertical bands within each segment. The system counts the number of hits identified in this vertical edge detection, prioritizes or orders these segments, and puts them on the stack with the highest ordered segment having the most hits or excessive gradients. This prioritizing and stacking is accomplished in step 160. Further, a loop counter is set in step 160 such that the number of target areas in the stack equals the loop count. The program then jumps in step 162 to jump point A-2 in FIG. 9 immediately preceding a convolute target step 132. The operator interactive program (FIG. 9) contains a series of steps, generally identified herein as the fine edge detection and target refinement routines, which are used in conjunction with target definition routines. The target definition routines are the operator interactive target definitions (the initial portion of FIG. 9), the sample search, vertical band search and horizontal band search routines. The target definition routines correspond to the target filter in FIG. 1.

Figure 13:
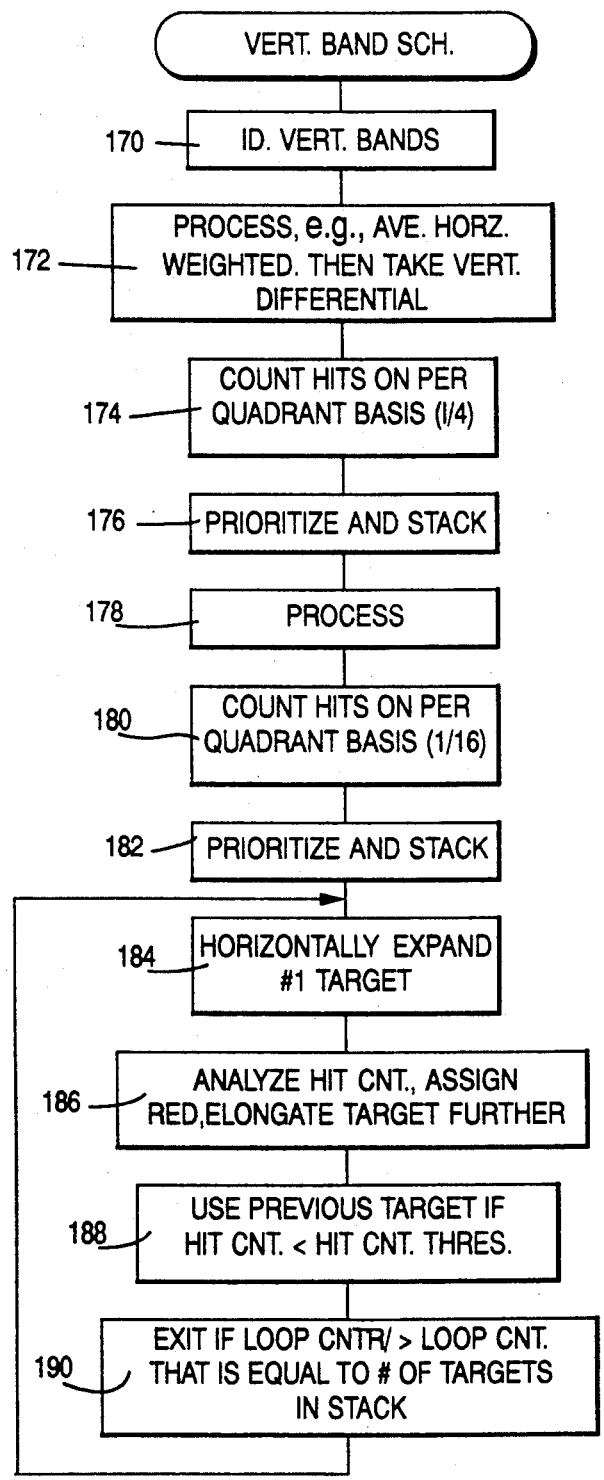
FIG. 13 is a flow chart illustrating the principal steps in a vertical band search routine.
Figure 14:
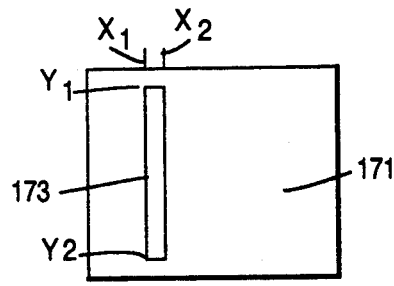
FIG. 14 is a graphic illustration of an input video and a vertical band target area.

FIG. 13 illustrates a flow chart showing the principal steps in a vertical band search. FIG. 14 graphically illustrates video image frame 171 and a single vertical band 173 which is one of a plurality of vertical bands defined on the frame. Vertical band 173 is approximately three pixels wide (X1-X2) and vertically spans approximately 20 percent of video frame image 171 (the distance between Y1 and Y2). As stated earlier, the upper and lower 10% of the frame image rarely depict blood vessels. In the vertical band search shown in FIG. 13, step 170 first identifies the plurality of vertical bands. A significant number of vertical bands can be identified and processed. In step 172, the system first electronically horizontally weights and averages the pixels and then takes a vertical differential, either the first, second or third differential as appropriate, between either vertically aligned pixels or vertically aligned groups of pixels. In step 174, the hits are counted in each vertical band. The hits correspond to gradients exceeding a pre-set level. The vertical bands are ordered based on hit count, and the first q vertical bands are put in the stack. Of those first ordered q vertical bands, the bands are divided into vertical quadrants and the hits are counted in each quadrant. The quartered vertical bands are then prioritized and stacked as shown in step 176. In step 178, the system further processes those sub-target areas and in step 180, the hits are counted in those sub-target areas on a further quarter sectional basis. In other words, the vertical bands are then divided into one-sixteenth areas and the hits are analyzed on that basis. In step 182, these one-sixteenth vertical band areas are ordered or prioritized and stacked.

Step 184 horizontally expands the first ordered sub-sub-target area and in step 186 that sub-sub-target area newly horizontally expanded is processed with a fine edge detection routine, the hit counts are analyzed, the color red is assigned to transitional pixels, and the target area is further horizontally elongated. In step 188, a determination is made if the previous target hit count is greater than the current hit count threshold. If so, the previous target is used. That is, if the sub-sub or one-sixteenth vertical band has a higher hit count than the elongated one-sixteenth vertical band target, than the system uses the originally identified one-sixteenth vertical band. Step 190 causes the system to exit this loop if the loop counter exceeds the loop count. The loop count, as described earlier, is equal to the number of targets in the stack. The loop counter is incremented each time the program goes through the fine edge detection routine, normally convolution, and does not develop a higher hit count for edge detection. The program then returns to a point immediately prior step 184 which calls for horizontally expanding the highest ordered target on the stack.

Figure 15:
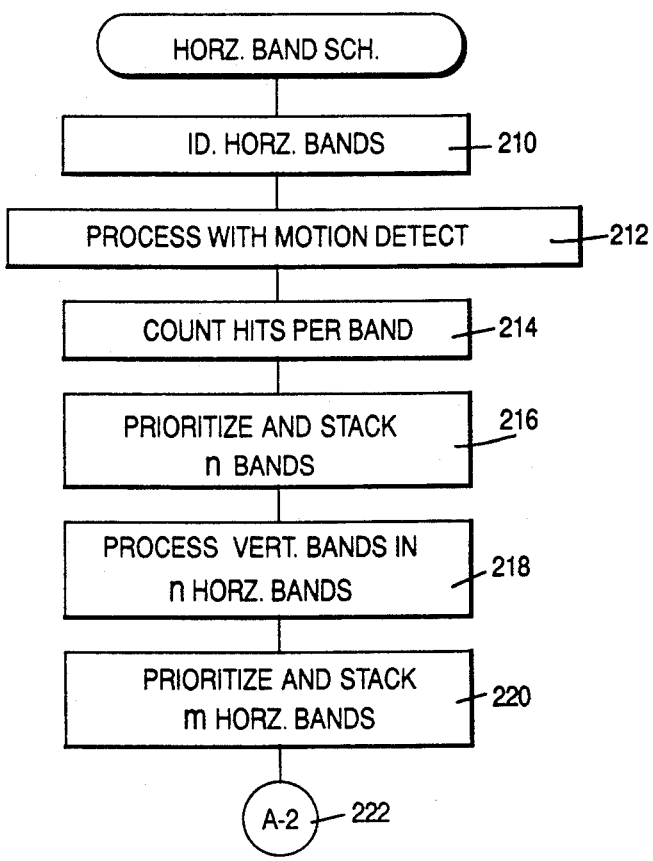
FIG. 15 is a flow chart showing the principal steps of a horizontal band search routine.

FIG. 15 illustrates a flow chart showing the principal steps in a horizontal band search. In step 210, horizontal bands of approximately 50 pixels in height are identified across the input video frame image. In step 212, the system detects motion within each horizontal band. Step 214 counts the number of hits or moving image blocks in each band, and in step 216, the bands are ordered or prioritized based on the number of moving image blocks per band. Only n horizontal bands are selected, n being equal to, for example, 4. In step 218, each n horizontal band is processed for edge detection in a plurality of vertical bands. These vertical bands may be three pixels wide and there may be 10 to 20 vertical bands within each n horizontal band. Step 220 prioritizes each horizontal band by counting the number of hits or transition pixels found in each vertical segment per each horizontal band and stacks m horizontal bands. The program in step 222 goes to jump point A-2 in FIG. 9 and the next step convolutes the highest ordered target as step 132 in FIG. 9.

Figure 5:
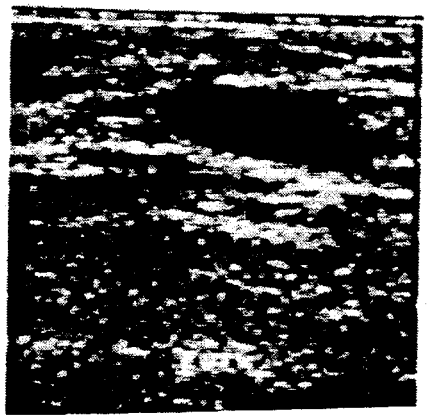
FIG. 5 is a photographic reproduction of a video image from an ultrasound scanner showing a transverse view of a vein.
Figure 16:
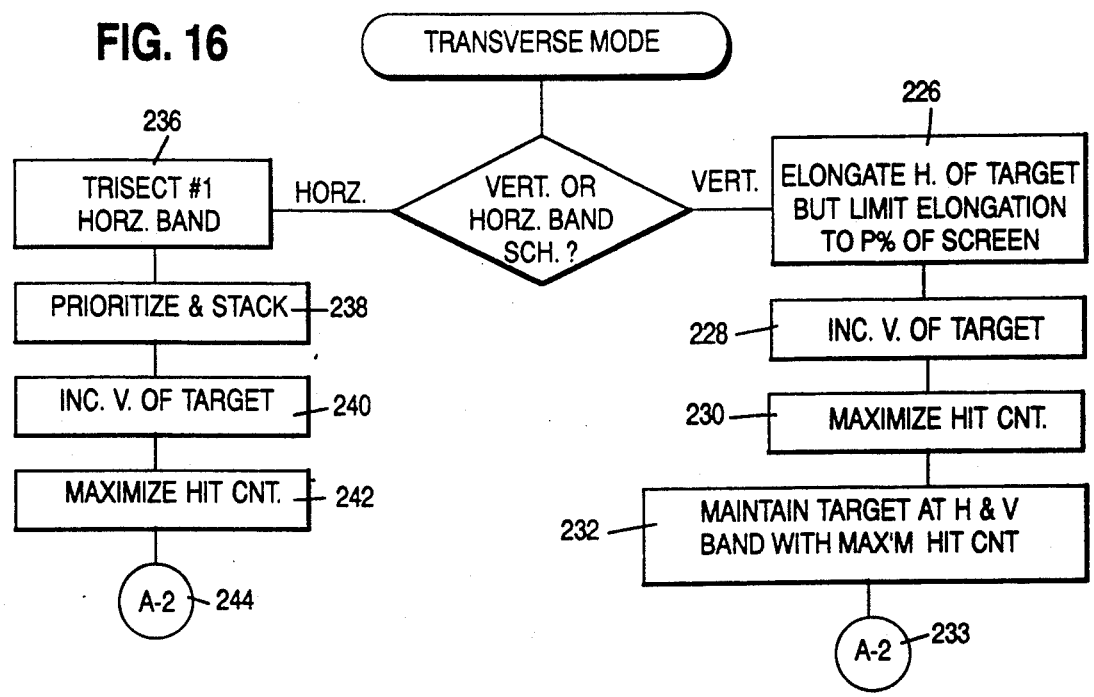
FIG. 16 is a flow chart showing the principal steps of a transverse mode routine; and, FIG. 17 is a flow chart showing the principal steps of an automatic detection routine.

FIG. 16 illustrates a flow chart showing the principal steps involved in a transverse mode routine. Preferably, the operator initially selects whether he or she is laterally viewing a vein with the ultrasound detector (FIG. 4) or whether he or she is transversely viewing the vein (FIG. 5). If the operator selects the transverse mode, decision step 142 in FIG. 9 calls up the transverse mode routine shown in FIG. 16. Decision step 224 determines whether a vertical band search has occurred earlier or a horizontal band search has occurred earlier. If a vertical search has occurred, step 226 of the routine horizontally elongates the target but limits that elongation to P% of the screen. In the transverse mode, a vein occupies a somewhat rectangular area somewhere on the screen as compared to the lateral view of the vein in which the vein extends horizontally across the screen. Therefore, in the transverse mode, one would limit the horizontal elongation of the target to a certain percentage of the screen, approximately 30 percent. In step 228, the vertical aspect of the target area is expanded or increased. As discussed above, a vertical band search utilizes vertical bands of one-sixteenth size in the target stack. This one-sixteenth vertical band height ma not be sufficient to fully capture the vertical expanse of the transverse view of the blood vessel. Therefore, step 228 increases that vertical height to a certain percentage, approximately 30 percent of the frame image. In step 230, the hit count is maximized. In other words, the horizontal and vertical expansion of the most probable target area is iteratively processed, that is, by increasing the dimension of the target area in one dimension until the hit count reaches a maximum, then stopping that incremental expansion and then incrementally expanding in the other direction of the target area until the hit count reaches the maximum. Step 232 maintains the target at the horizontal and vertical expanse with the maximum hit count. Jump step 233 causes the program to jump to jump point A-2 in FIG. 9 immediately preceding the convolute target area step 132.

Returning back to decision step 224, if a horizontal band search has been conducted earlier, step 236 trisects the highest ordered horizontal band on the target stack. As discussed above with respect to FIG. 15, m horizontal bands are in the target stack and the highest ordered horizontal band has already been processed. By trisecting the highest order horizontal band, counting the transitional pixels in that band, and ordering and stacking those band segments in step 238, the system has then identified the most likely transverse vein area within that horizontal band target area. In step 240, the vertical aspect of the target area is increased and in step 242, the hit count is maximized while increasing the vertical aspect. Step 244 jumps the program to jump point A-2 in FIG. 9 immediately preceding the convolute target area number one in step 132.

Of course, different percentages for segmenting vertical and horizontal bands could be utilized in the vertical band search, horizontal band search and transverse mode routines dependent upon the speed of the microprocessor, the speed at which the operator wishes the system to identify and video highlight the vascular walls and the particular edge detection routine selected and installed as part of the system the various procedures discussed above.

FIG. 17 illustrates a flow chart showing the principal steps in an automatic system. In step 310, a timer is set. The timer is either a count up or a count down timer. In step 312, the operator interactive program (FIG. 9) is called and executed by the microprocessor. In decision step 314, a determination is made whether the target is moved. If the operator has moved the target, step 316 resets the timer and returns the program to a point immediately preceding the execute operator interactive step 312. If the target is not moved, a decision is made in step 318 whether the timer has timed out. If not, the program returns to the operator interactive program already in progress. If the timer has timed out, the yes branch is taken and decision step 320 is encountered which determines whether the operator has previously selected the transverse mode detection. If the yes branch is taken, step 322 resets the timer.

The automatic program then calls up the vertical band search program in step 324. In step 326, a determination is made whether the hit count found during the vertical band search exceeds an automatic threshold. If it does, the automatic program resets the timer by returning in a feedback loop to a point prior to step 322. If the hit count in the vertical search band program does not exceed the automatic threshold, the no branch is taken and a determination is made in step 328 whether the timer has timed out. If not the program returns back to the vertical band search. If the timer has timed out, the yes branch is taken and the timer is reset in step 330. In step 332, the sample search routine is executed. In decision step 334, a determination is made as to whether the hit count obtained from the sample search exceeds the automatic threshold. If it does, the program returns, resets the timer and further executes the sample search. If it does not, the program then determines whether the timer is timed out in decision step 336. If it hasn't, the program returns and further executes the sample search. If the timer has timed out, step 338 resets the timer and then executes in step 340 a horizontal band search. Decision steps 342 determine whether the hit count from the horizontal band search has exceeded the auto threshold value and in decision 344 a determination is made whether the timer is timed out. If the hit count is greater than the auto threshold, the automatic program remains in the horizontal band search. If the timer times out and the hit count is less than the automatic threshold, the automatic program then displays in step 346 "no vessel found." If the timer has not timed out, the automatic program remains in the horizontal band search.

In summary, the automatic program first places the step of limiting the target area under the control of the physician or operator for a predetermined period of time set by the timer. If the operator or physician moves the target, the timer is reset and the system continues to search for the blood vessel in that particular region. If the operator does not move the target and the timer has timed out, and if the operator has previously selected the transverse mode, the next preferred search routine is the vertical band search. This search is followed by a sample search and the horizontal band search. If during any one of these three searches the hit count exceeds the automatic threshold, the automatic program stays within that particular routine since that routine has been successful in detecting a relatively large number of transitional pixels corresponding to detected edges or vascular walls. If the particular routine does not find enough transitional pixels (hit counts), and the timer times out, the automatic program switches to the next program.

If the no branch is taken from decision step 320, the transverse mode decision, the timer is reset in step 350. In step 352 a sample search is executed. In decision step 354, a determination is made whether a good hit count has been obtained or whether the timer has timed out. If a good hit count was obtained, the yes branch is taken from decision step 354. If the timer has not timed out, the yes branch is also taken. If either one of these conditions is false, that is a poor hit count or a time-out of the timer, the no branch is taken, and in step 356, the timer is reset. Step 358 executes the vertical search routine, and in decision step 360, a determination is made whether a good hit count has been obtained or whether the timer has timed out.

If the no branch is taken, the timer is reset in step 362, horizontal band search is executed in step 364 and in decision step 366 a determination is made whether the hit count exceeds the automatic threshold or whether the timer is timed out. If the hit count has not exceeded the automatic threshold or if the timer has timed out, the program displays "no vessel found" in step 346.

There are several features that the operator or physician could select at the initiation of the program. The following Operator Selectable Variable Table illustrates some of the features. The selection is made in a menu driven format.

OPERATOR SELECTABLE VARIABLES TABLE

1. Time in time-based comparison for motion detection.
2. Sensitivity switch—hit count threshold, if auto, auto threshold
3. Search routine preference table auto threshold
4. Acceleration mode—in auto, decrement timer clock and auto threshold
5. Manual
   a. Select search routine
   b. Change hit count threshold
   c. Change size of initial target area
      i. Operator Interactive
      ii. Vertical band width
      iii. Horizontal band height With respect to the operator selecting a time in the time based comparison for motion detection, by selecting the time or the number of frames for each time-based comparison, the operator adjusts the system to match or estimate the speed of blood flow through the blood vessel. The system could be further expanded such that the doctor could input, for example, blood pressures and the system could compute from the blood pressures or other physical data the speed of the blood through the blood vessel. The system then the appropriate time from a look-up table based on the input physical parameter. With respect to variable 2 above, by changing the hit count threshold or the automatic threshold, the operator determines how long the system will remain in a particular search routine (the automatic routine) and whether the system will mark transitional pixels when a low hit count is encountered. See for example step 134 in FIG. 9 above. The search routine preference table simply provides the operator with the ability to reorder the searches identified in the automatic routine. Rather than initially starting with the operator interactive program and then proceeding with the sample search, vertical search and horizontal search in a non-transverse mode, the operator may wish to reorder the searches to have the operator-interactive first, the horizontal search, the vertical search and ending with the sample search. When the physician or operator selects the acceleration mode (item 4 above), the timer in the automatic mode would be set lower and hence each search routine would be executed for a shorter period of time. Also, in the acceleration mode, the operator or physician can change the automatic threshold. By raising the automatic threshold, the system would not linger in a particular search routine. Lastly, in the manual mode, the operator or physician can manually select a particular routine or could change the hit count for that particular routine or could change the initial target area in the interactive, vertical band or horizontal band search. Of course, other system parameters can be set by the operator or physician because the foregoing selectable variables are simply exemplary.

The claims appended hereto are meant to cover modifications and changes within the scope and spirit of the present invention.

What is claimed is:

1. An apparatus for detecting blood vessels and displaying enhanced video images thereof based upon video images of an ultrasound scanner of subcutaneous blood vessels comprising:
    means for receiving an input video image from said video images of said ultrasound scanner of subcutaneous blood vessels;
    an edge detector, coupled to said means for receiving, sensing gradients in pixel values in a predetermined portion of said input video image and marking transitional pixels at predetermined gradients representing at least a portion of a vascular wall about a lumen of a blood vessel; and
    means for concurrently displaying said video images of said ultrasound scan end the marked transitional pixels, said marked pixels being displayed in a contrasting color compared to the concurrently displayed images from said ultrasound scanner,
    wherein said video images from an ultrasound scanner are a sequential plurality of scan video images, said means for receiving, edge detector and means for displaying utilizing a sequential plurality of input video images, corresponding to said plurality of scan video images, and said edge detector marking respective, sequential transitional pixels for at least predetermined, periodic ones of said sequential plurality of input video images; said means for displaying overwriting intermediate ones of said sequential plurality of input video images with the marked sequential transitional pixels.

2. An apparatus as claimed in claim 1 including a pixel averager coupled to said means for receiving and said edge detector, said pixel averager averaging pixel values over at least a predetermined horizontal range and assigning a discrete average pixel value to each pixel in said predetermined portion of said input video image, said edge detector utilizing said average pixel values.

3. An apparatus as claimed in claim 1 wherein said predetermined portion of said input video image is a target area, the apparatus including an operator controlled means for moving said target area within said input video image wherein said edge detector initially operates on pixels within said target area.

4. An apparatus a claimed in claim 1 wherein said predetermined portion of said input video image is a plurality of discrete target areas, said edge detector includes means for determining pixel value gradients exceeding a gradient threshold between one of vertically adjacent pixels and vertically adjacent, horizontally averaged groups of pixels and includes means for identifying pixels at the excessive gradients and marking the same as transitional pixels.

5. An apparatus as claimed in claim 4 including processing means for ordering said plurality of target areas based upon the number of transitional pixels in each target area and for controlling said edge detector such that further analysis occurs on pixels located in an ordered target area with the greatest number of transitional pixels.

6. An apparatus as claimed in claim 5 wherein said further analysis by said edge detector utilizes means for convoluting individual pixels with predetermined neighboring pixels within said ordered target area and for identifying convoluted pixel value gradients exceeding a further gradient threshold, said edge detector only marking transitional pixels associated with such excessive gradients.

7. An apparatus as claimed in claim 1 wherein said video images from an ultrasound scanner are a sequential plurality of scanner video images, said means for receiving utilizing a sequential plurality of input video images, corresponding to said plurality of scan video images, the apparatus including a motion detector coupled to said means for receiving and said edge detector, said motion detector correlating in time and space blocks of averaged pixels and identifying moving image blocks within pre-established portions of said sequential plurality of input video images; said apparatus including means for defining said predetermined portion of said input video image based upon the identified moving image blocks.

8. An apparatus as claimed in claim 7 wherein said pre-established portions are sample regions in said input video image; said means for defining including means for ordering a first plurality of target areas in a first input video image based upon the number of identified moving image blocks in each target area and for assigning an ordered target area having the greatest number of identified moving blocks as said predetermined portion of said input video image for said edge detector.

9. An apparatus as claimed in claim 7 wherein said preestablished portions are a plurality of pre-established portions in each said input video image; said means for defining including means for ordering said pre-established portions based upon the number of identified moving image blocks in each pre-established portion within a first input video image and for assigning an ordered pre-established portion having the greatest number of identified moving blocks a said predetermined portion of said input video image for said edge detector.

10. A method for detecting blood vessels and displaying enhanced video images from video images obtained from a ultrasound scan of subcutaneous blood vessels comprising the steps of:

obtaining at least one electronic representation of said video image from said video images of an ultrasound scan of said blood vessels;

identifying gradients in pixel values in the electronic video image exceeding a predetermined gradient representing vascular walls about a lumen of said blood vessel;

electronically marking transitional pixels at those excessive gradients; and, concurrently displaying said video images of said ultrasound scan and the marked transitional pixels, said marked pixels displayed in a contrasting color compared to the concurrently displayed video images.

11. A method as claimed in claim 10 wherein the step of obtaining includes obtaining a plurality of sequential scan video images and wherein the the steps of identifying, marking and displaying are electronic processing steps which occur substantially in real time.

12. A method as claimed in claim 10 wherein the step of identifying gradients is limited to a target area in said electronic video image.

13. A method as claimed in claim 12 wherein the step of identifying gradients is a step of identifying high level gradients and said predetermined gradient is high level predetermined gradient, and the method includes the steps of:

electronically identifying a plurality of target areas in said electronic video image;

identifying low level gradients in pixel values and the associated pixels in each of said plurality of target areas exceeding a low predetermined gradient, said low predetermined gradient being less than said high level predetermined gradient;

ordering said plurality of target areas by associated pixel counts in each target area with a highest order target area having the most associated pixel count therein; and, wherein said steps of identifying target areas, identifying low level gradients, and ordering target areas occurring prior to the step of identifying high level gradients, and the step of identifying high level gradients utilizes only a portion of said electronic video image within said highest order target area.

14. A method as claimed in claim 13 wherein the step of identifying high level gradients convolutes a group of neighboring pixel values with a primary pixel value and determines whether the convoluted pixel exceeds a predetermined threshold and the step of marking operates on pixels having convoluted values exceeding said threshold.

15. A method as claimed in claim 14 wherein the step of obtaining includes obtaining a plurality of sequential scan video images and wherein the steps of identifying target areas, identifying low level gradients, ordering said target areas, identifying high level gradients, marking the pixels and displaying are electronic processing steps which occur substantially in real time.

16. A method as claimed in claim 10 wherein the step of obtaining includes obtaining a plurality of sequential scan video images, and the method includes the steps of:

electronically identifying a plurality of time based sequential target areas in each of said plurality of sequential video images;

electronically detecting spatially moving image blocks in each of said plurality of sequential target areas, counting the number of each moving image blocks within each target area in a first electronic video image;

ordering said plurality of target areas in said first electronic video image with a highest order target area having the highest number of moving image blocks therein; and, wherein said steps of identifying target areas, detecting moving blocks, and ordering target areas occurs prior to the step of identifying gradients, and the step of identifying gradients utilizes only portion of said first electronic video image within said highest order target area.

* * * * *